(12) United States Patent
Hubner et al.

(10) Patent No.: US 6,638,066 B2
(45) Date of Patent: Oct. 28, 2003

(54) DENTAL VACUUM SYSTEM

(75) Inventors: Henry Hubner, Amityville, NY (US);
Edgar Alzner, Garden City, NY (US);
Selwyn Foster, Jr., Laurelton, NY (US)

(73) Assignee: Air Techniques, Inc., Hicksville, NY (US)

( * ) Notice: Subject to any disclaimer, the term of this patent is extended or adjusted under 35 U.S.C. 154(b) by 0 days.

(21) Appl. No.: 10/039,418

(22) Filed: Jan. 4, 2002

(65) Prior Publication Data

US 2003/0129561 A1 Jul. 10, 2003

(51) Int. Cl.⁷ ............................................... A61C 17/14
(52) U.S. Cl. ........................................................ 433/92
(58) Field of Search ................................ 433/92, 91, 96

(56) References Cited

U.S. PATENT DOCUMENTS

| | | | |
|---|---|---|---|
| 3,051,175 A | * | 8/1962 | Nugent .......................... 604/65 |
| 3,078,579 A | * | 2/1963 | Jones et al. .................... 433/92 |
| 3,305,927 A | * | 2/1967 | Mitchell ........................ 433/92 |

* cited by examiner

*Primary Examiner*—Kevin Shaver
*Assistant Examiner*—Melba Bumgarner
(74) *Attorney, Agent, or Firm*—Louis E. Marn; Clifford G. Frayne

(57) ABSTRACT

A dental vacuum system for use in dental operatories in which a dental aspirator tip in the dental operatory is in fluid communication with a two stage side channel blower for providing suction to the system, there being interposed between the dental aspirator tip and the two stage side channel blower, a solid debris collector and separation chamber for the passage of air and collection of effluent and debris, the air outlet port in the separation chamber having a float valve sealing means, the float valve sealing means having a pivotal lever with a sealing means at one end for engagement with the air outlet port and a float at the opposing lever end for contact with a fluid or foam level within the separation tank, the float depending from the lever end a sufficient distance so as to cause the sealing means to seal the outlet port before any foam can exit the separation tank.

12 Claims, 5 Drawing Sheets

DENTAL VACUUM SYSTEM

BACKGROUND OF THE INVENTION

1. Field of the Invention

The present invention relates to dental care facilities and in particular to a central vacuum system for dental care operatories.

RELATED APPLICATIONS

This application claims the benefit of provisional application 60/271,069 filed Feb. 26, 2001.

2. Description of the Prior Art

Modern dental facilities usually include multiple operatories and a central vacuum system. Dental aspirator tips are provided at each operatory for disposition in the patient's oral cavity to remove aerosols, liquids, solid debris and odors from the patient's mouth. Typical conventional dental vacuum systems have been far from ideal from the standpoints of noise output, vacuum intensity and flow rate characteristics, efficiency and reliability. Typical commercially available dental vacuum systems include a water ring or turbine vacuum pump and a back up pump is normally specified because of the known unreliability of such pumps.

The unreliability of some pumps utilized in the dental vacuum system is the result of the poor design of the overall dental vacuum system which allows aerosols, liquids and solid debris to pass through the separation chamber where it is designed to be retained, entrapped, and drained, and contact the vacuum pump thereby causing damage to the pump and the overall operation of the dental vacuum system.

One primary cause of damage to the pump in a dental vacuum system presently used is that the separation chamber utilizes a float valve in the form of a ball within a mesh cage to seal the outlet of the separation chamber. With the advent of new liquids and aerosols used in the dental operatory, a foam is generated within the separation chamber. The float valve in the form of a ball within a mesh cage is designed to cause the ball to rise and seal the outlet under the influence of liquid. Oftentimes the foam is generated to such an extent that it rises to the height of the outlet, but the density of the foam is insufficient to raise the ball within the mesh cage to seal the outlet. Thus foam and possible other light debris are removed from the separation chamber and introduced to the pump. The present invention seeks to eliminate this possibility.

OBJECTS OF THE INVENTION

An object of the present invention is to provide for a novel dental vacuum system for the efficient evacuation of aerosols, liquids, solid debris and odors from the patient's mouth in a dental operatory.

Another object of the present invention is to provide for a novel dental vacuum system having an improved separation tank design in which the manner of introduction of air and effluent provides for self-cleaning of the interior walls of the separation tank.

A further object of the present invention is to provide for a novel dental vacuum system utilizing a two stage side channel blower for improved vacuum within the system and adaptive to older systems having small diameter piping.

A still further object of the present invention is to provide for a novel dental vacuum system having a novel separation tank and float valve mechanism which eliminates the possibility of foam or other liquid from entering the air outlet port of the separation tank and thus enter the inlet of the vacuum pump.

SUMMARY OF THE INVENTION

A dental vacuum system for use in dental operatories in which a dental aspirator tip in the dental operatory is in fluid communication with a two stage side channel blower for providing suction to the system, there being interposed between the dental aspirator tip and the two stage side channel blower, a solid debris collector and separation chamber for the collection of debris and effluent, the air outlet port in the separation chamber having a float valve sealing means for the air outlet port, the float valve sealing means having a pivotal lever with a sealing means at one end for engagement with the air outlet port and a float at the opposing lever end for contact with a fluid or foam level within the separation tank, the float depending from the lever end a sufficient distance so as to cause the sealing means to seal the outlet port before any foam can exit the separation tank.

DETAILED DESCRIPTION OF THE DRAWINGS

Figure 1:
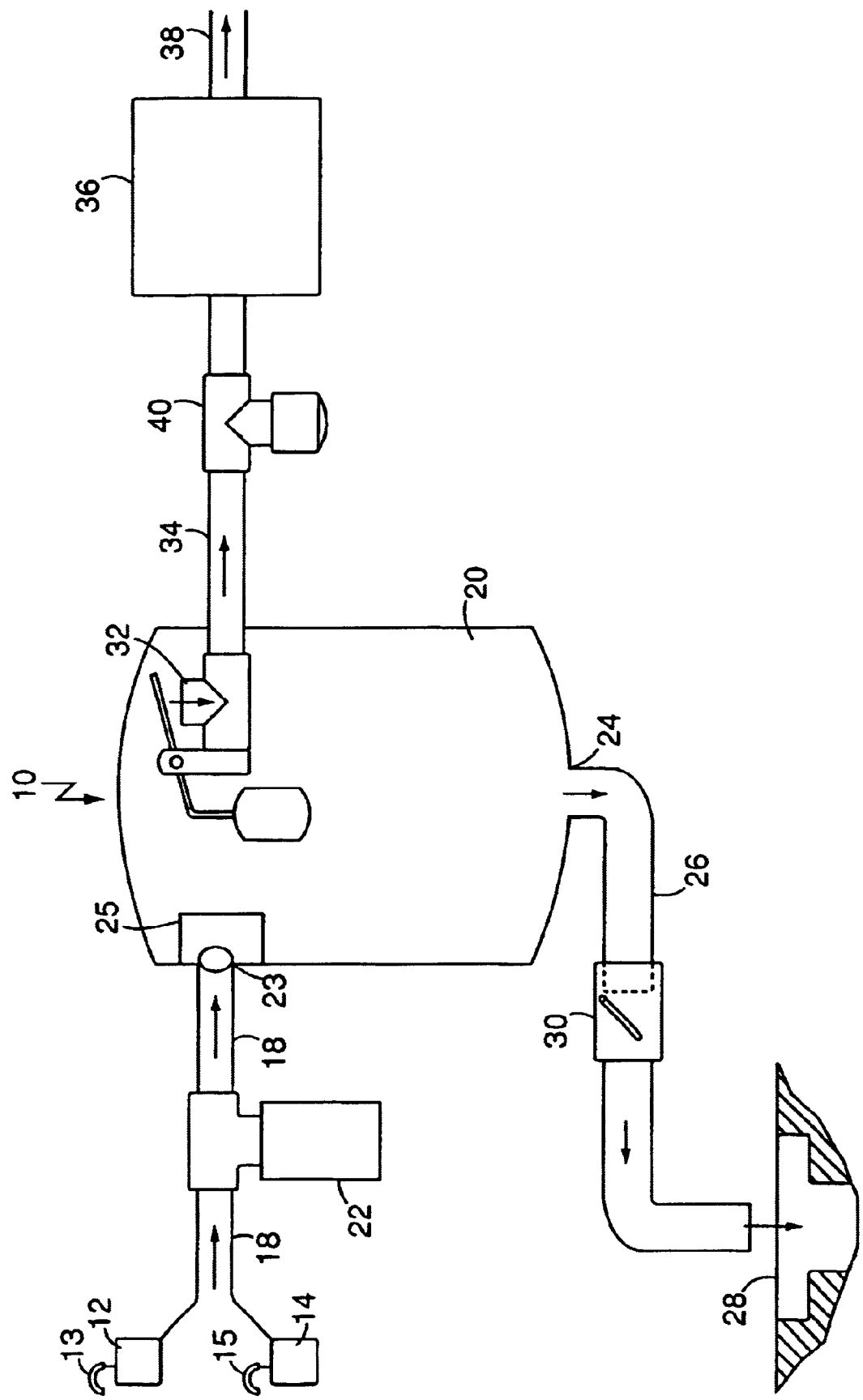
FIG. 1 is a flow diagram of the overall dental vacuum system of the present invention.

FIG. 1 is a flow diagram of the dental vacuum system 10 of the present invention. During the course of a dental procedure, gases, liquids and solids are removed from each dental operatory 12 and 14, by means of a dental aspirator tip 13 and 15 which are disposed within the patient's oral cavity. Gases, liquids, and solids under vacuum or suction are transported via conduit 18 to a separation tank 20. Disposed in conduit 18 prior to the separation tank 20 is an optional solids collector 22 which allows gas and liquids to pass through, but interrupts the flow of most heavier solids and causes them to be deposited in the collector. The solids collector 22 may be eliminated from the system and solid debris may be collected with effluent in the separation tank 20. In this embodiment the gas, liquids and solids are introduced into the separator tank 20 through inlet port 23 wherein the liquids and debris accumulate in the bottom of the tank and are subsequently drained through drain outlet 24 through conduit 26 to a sewer drain 28. A check valve 30 is positioned in conduit 26 to prevent any back flow.

The gas introduced into separation tank 20 exits separation tank 20 through a gas or air outlet port 32 to exit conduit 34 which is in communication with the vacuum pump 36 which provides the vacuum and suction to the overall system. The gas thus drawn through the system is then evacuated to the atmosphere through conduit 38. There is positioned between separator tank 20 and a vacuum pump 36 a vacuum relief valve 40. It is the intent of this design that only air or gases exit air outlet port 32 to exit conduit 34 and hence vacuum pump 36.

Figure 5:
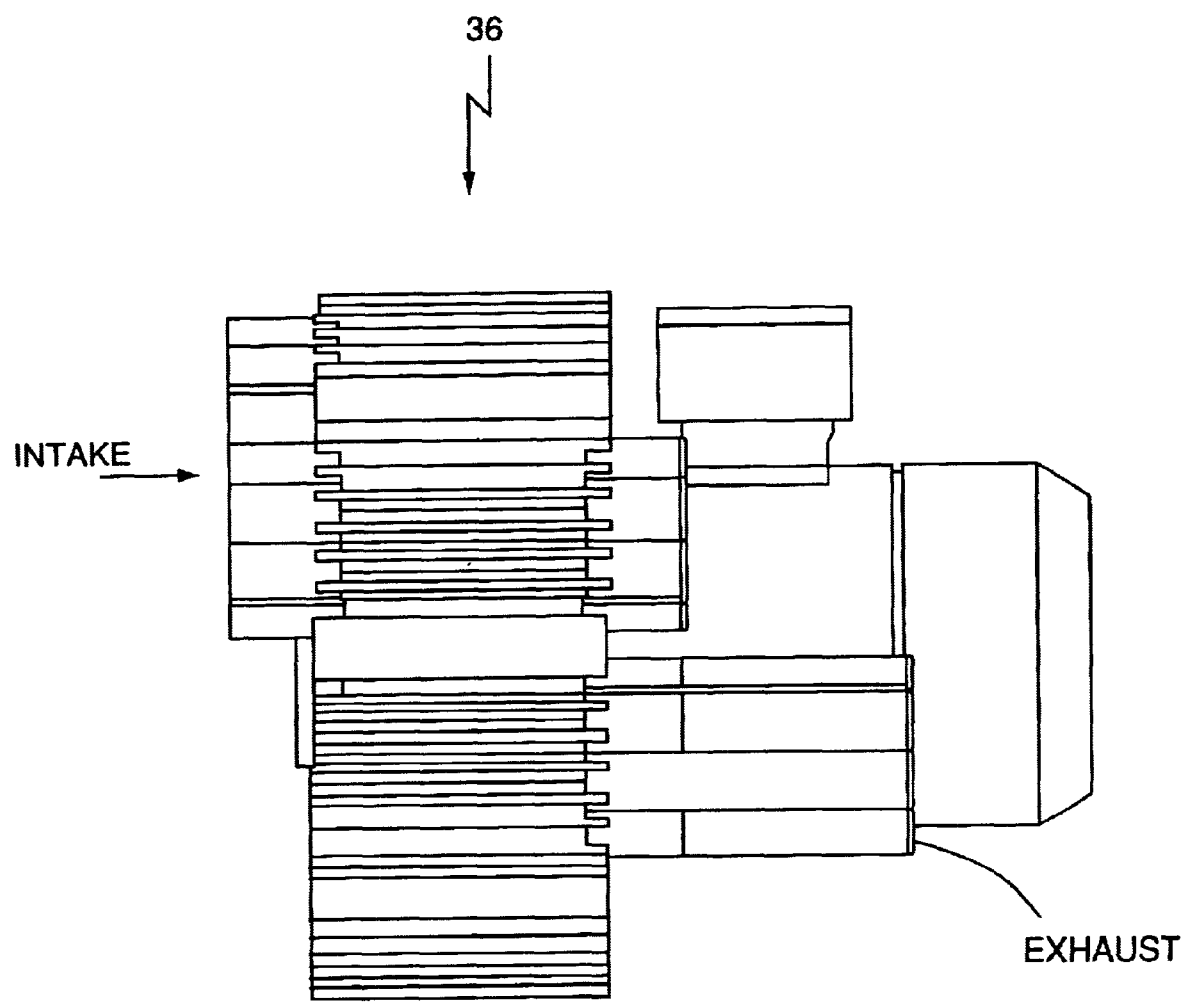
FIG. 5 is a side view of the vacuum means of the present invention.

The preferred vacuum pump 36, FIG. 5, utilized in the vacuum system is a side channel two stage blower having an open impeller with a diameter of approximately 11 inches. The side channel two stage blower serving as vacuum pump 36 in the system produces usable flow at 12 inches of mercury and a maximum vacuum of 17 inches of mercury at no flow. This provides the advantage in dental applications to increase the flow and vacuum levels and allows the installation of the vacuum pump 36 in drop ceilings up to ten feet above the operatories thus permitting increased floor space for the operatories in the dental office. Additionally with the increased flow and vacuum levels, it is adaptable to work in pre-existing installations where piping diameters between the operatory and the separator tank may be less than desirable. An example of a suitable vacuum pump or vacuum source would be Siemens two stage regenerative blower model 2BH7320.

Figure 2:
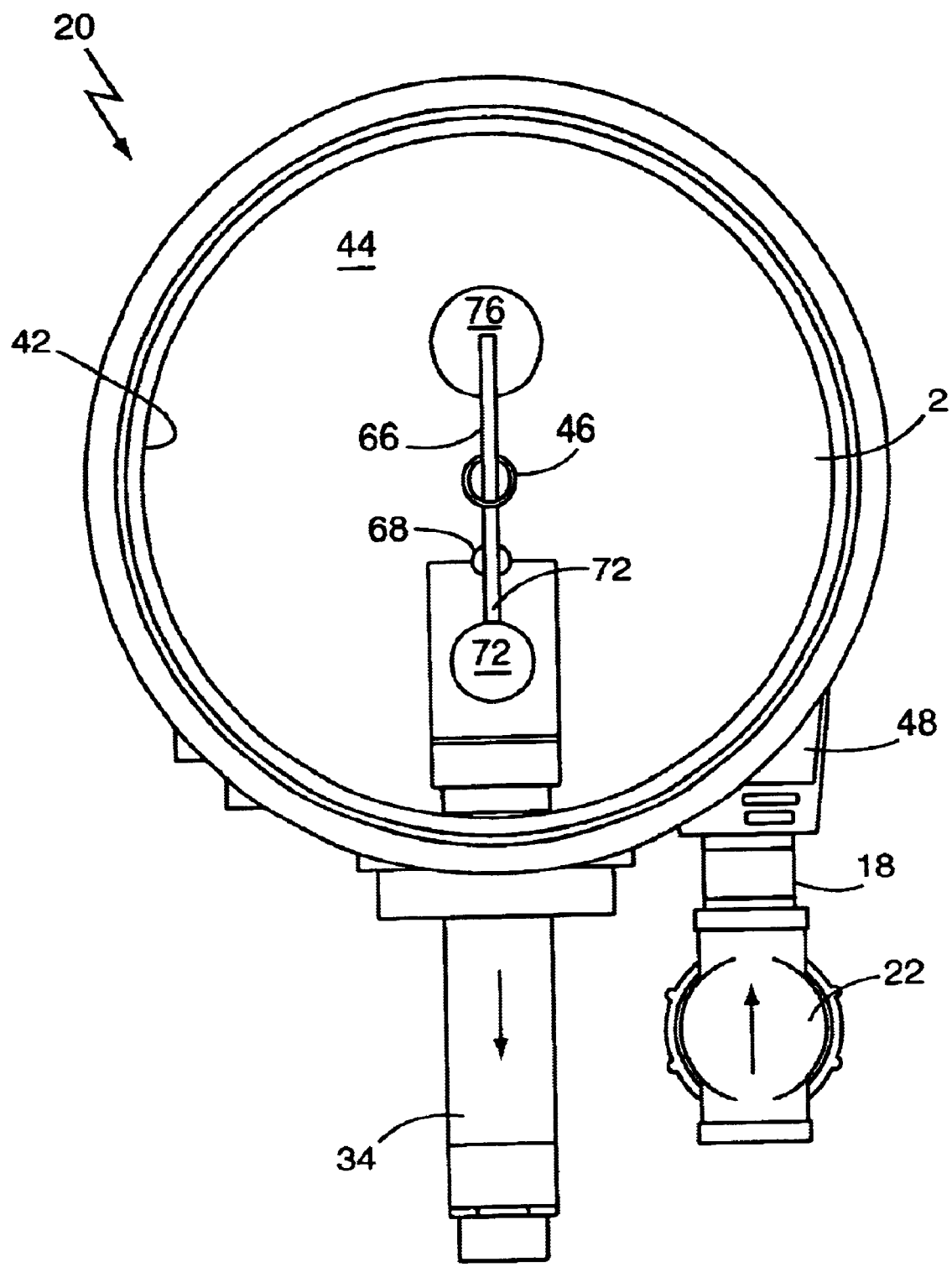
FIG. 2 is a top view looking downwardly into the interior of the separation tank along plane 2—2 of FIG. 1.

FIG. 2 is a top view of a separator tank 20 of the present invention along plane 2—2 of FIG. 1 illustrating an improved design for the introduction of the gas and effluent to the separator tank 20. The separator tank 20 is generally cylindrical in shape having an inner side wall 42, a conically-shaped bottom wall 44, and a drain 46 centrally positioned at the lowest point of the conically-shaped bottom wall 44.

The use of aerosols and other liquids in the dental operatory will oftentimes result in separation tank having a level of liquid overlaid with a layer of foam. Upon draining, the foam layer may leave a film on the inner side wall 42 of separator 10 and on the bottom sloped wall 44 of separator tank 10. Most separator tanks in use in dental applications use a conduit and an entry port to introduce the gas and effluent into the separator tank which is at a right angle to the tank wall. The problem with this construction is that the air and effluent stream flow into an open space and may even strike the interior wall 42 of separator tank opposite the inlet port. This can lead to areas of no or low flow velocities which permit the accumulation of sediments or the foam problem previously stated.

One option available with Applicant's separation tank is a tangential entry for the air and effluent stream. After passing through the solids collector 22 in conduit 18, the conduit is secured to a tangential entry port 48 which introduces the air and effluent tangential to the inner wall 42 of separator tank 20. This minimizes splashing and causes the liquid and aerosol to coalesce and drop to the bottom of the tank. It also introduces a helix-like circular flow, a downward spiral along the inner side wall 42 of separator tank 20 which continues to the bottom and tends to flush sediments and film from the tank wall in the bottom. Another option as illustrated in FIG. 1 would be to position a baffle means 25 on the inside of separation tank 20 spaced apart from the inlet port 23 to disrupt the flow into the separation tank by direction it to the sides of the baffle means 25.

Figure 3:
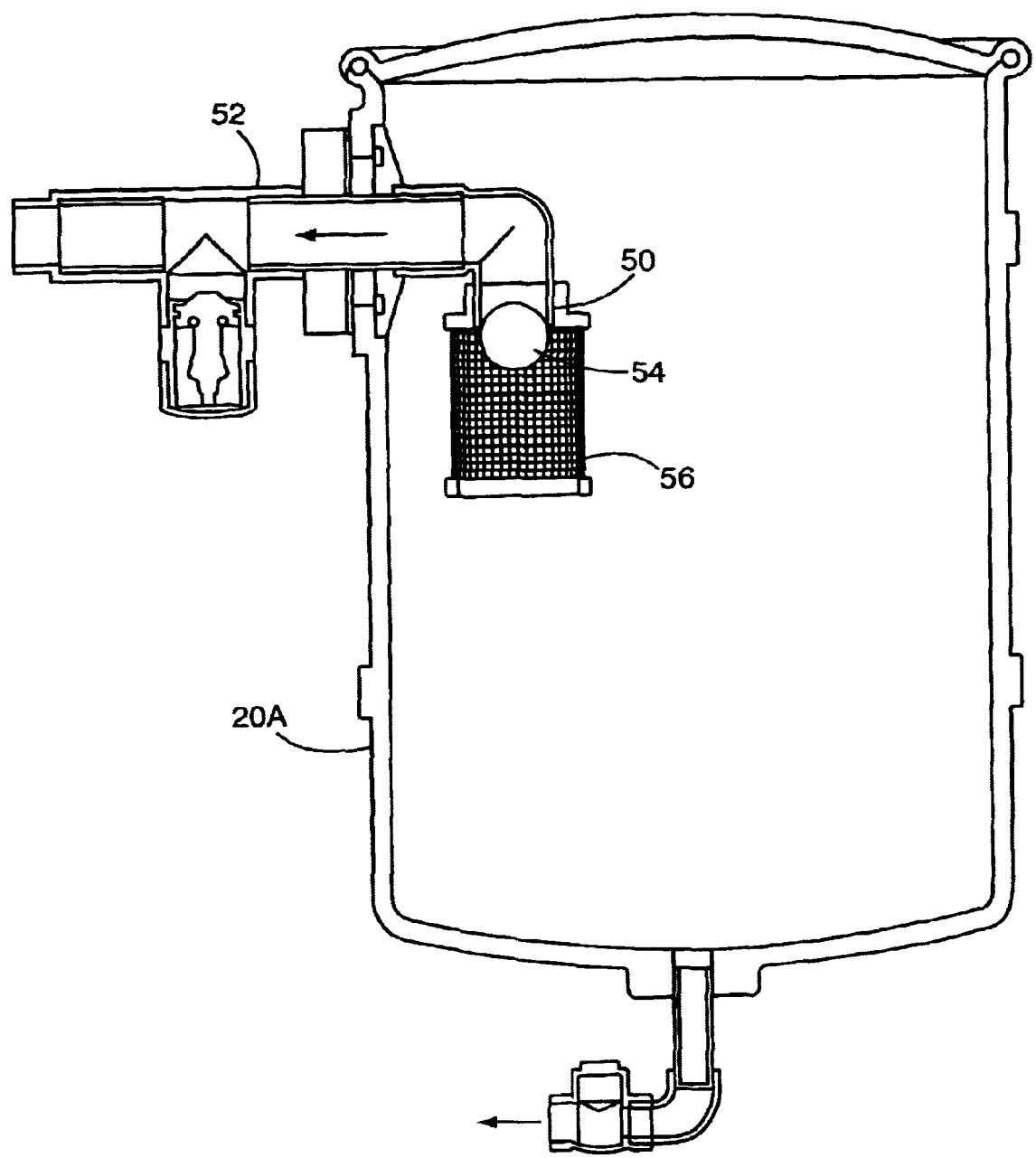
FIG. 3 is a side cross-sectional view of the separation tank of the Prior Art.

FIG. 3 is illustrative of the prior art regarding separator tanks 20A. The prior art design suffers from deficiencies as a result of the use of certain liquids and aerosols in the dental operatory. In the design illustrated in FIG. 3, the air outlet port 50 leading to exit conduit 52 and thence to a vacuum pump (not shown) is controlled by a floating ball valve 54 positioned within a mesh cage 56. If liquids were to accumulate in the separation tank 20A and rise to a level proximate the air outlet port 50, the liquid would raise the floating ball valve 54 within the mesh cage 56 to seal the air outlet port 50 before liquid could be sucked out of the separation tank and introduced into the vacuum pump. The operation of the vacuum pump and its operative parts are easily damaged by the introduction of liquid into the pump. Thus the ball float is a safety feature to protect the vacuum pump. However, with the introduction of certain liquids and aerosols as previously discussed into the dental operatory, the contents of the separation tank 20A often consists of liquid and foam. It is thus possible that the liquid level in the separation tank may be well below the air outlet port 50, but that the foam layer approaches or exceeds the air outlet port 50. The foam does not have the necessary density to engage the floating ball valve 54 and lift it into sealing contact with air outlet port 50. The foam is thus sucked from the separation tank to the vacuum pump which is extremely undesirable.

Figure 4:
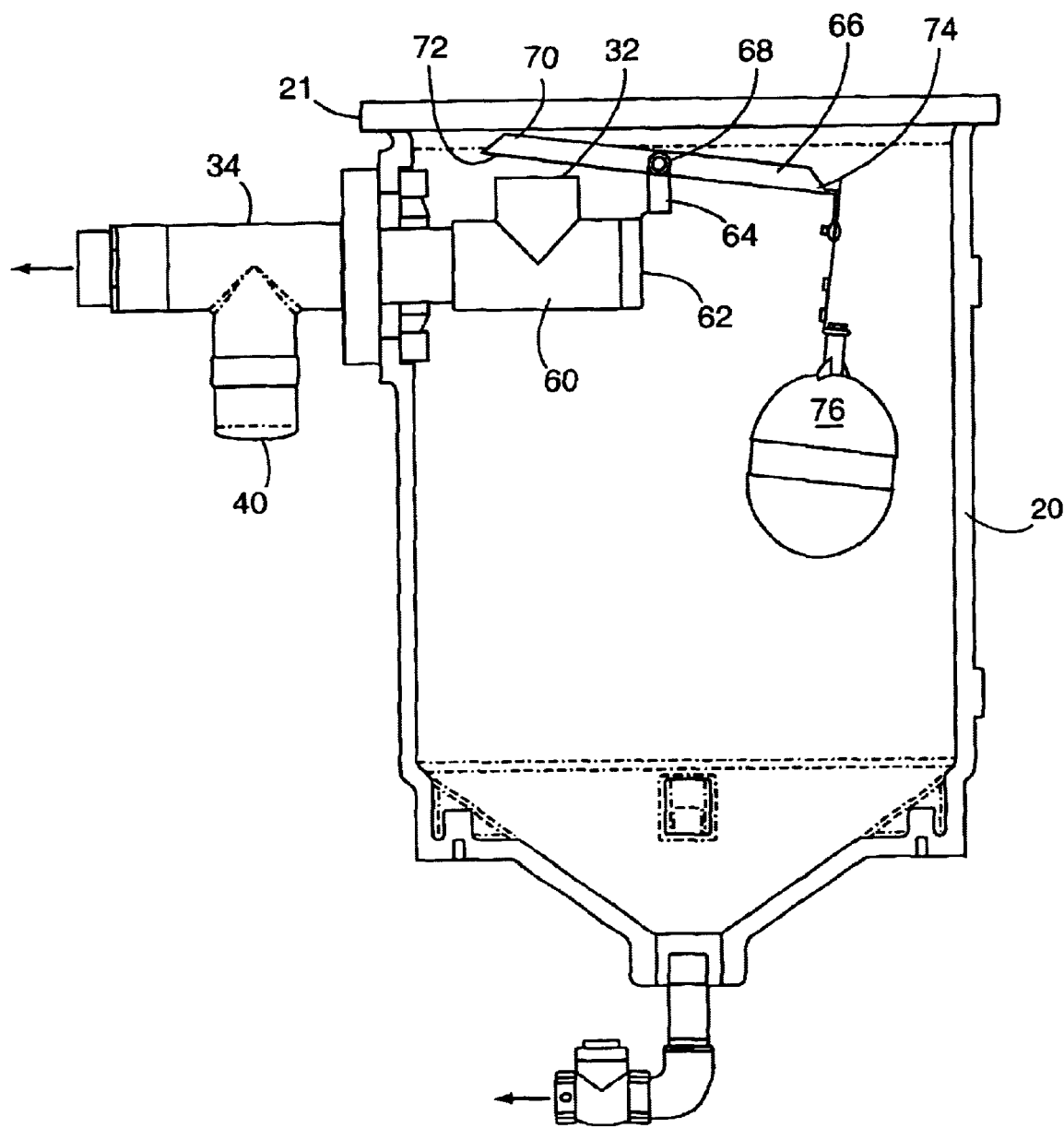
FIG. 4 is a side cross-sectional view of the separation tank and sealing means of the present invention.

FIG. 4 illustrates the Applicant's modification to the separation tank 20 of the instant invention to accommodate a sealing means for the air outlet port 32 which takes into consideration the possibility of a foam layer within the separation tank.

FIG. 4 is a cross-sectional view of separation tank 20 as illustrated in FIG. 1. In this configuration, air outlet port 32 is positioned proximate the lid 21 of the separation tank 20. The air outlet port 32 is oriented to face upwardly towards lid 21. Air outlet port 32 is in communication with conduit 34 which is in communication with vacuum pump 36 (not shown). Air outlet port 32 is incorporated in a sleeve which is secured to an extension of conduit 32 within the separation tank 20. Secured to this sleeve 60 at its terminus 62 is a lever support 64 having positioned thereon, a pivot lever 66 mounted at pivot point 68. A first end 70 of pivot lever 66 incorporates a seal 72 cooperative with air outlet port 32 to effect the closure of air outlet port 32 under certain desired conditions.

Secured to a second end 74 of pivot lever 66 is a float 76 mounted in depending relationship to pivot lever 66. The distance that the float 76 depends from pivot lever 66 is adjustable. It is positioned below the pivot point 68 and insures that the closure of air outlet port 32 will be effectuated by pivot lever 66 and seal member 72 before any foam can be introduced into conduit 32 and thus to the vacuum pump.

The design of the separation tank as illustrated in FIG. 4 insures that no foam or other light solid debris can be removed through air outlet port 32 and conduit 34. This can be accomplished in several ways. The distance that float 76 depends from pivot lever 66 can be adjusted to insure that it is engaged by the fluid level well before any overlying foam layer that reaches air outlet port 32. Alternatively, the weight of the float 76 can be adjusted such that the density of the foam is sufficient to raise float 76 and seal air outlet port 32 without requiring the float 76 to be moved by the density of the fluid.

While the present invention has been described with respect to the exemplary embodiments thereof, it will be recognized by those of ordinary skill in the art that various modifications can be made without departing from the spirit and scope of the invention. Therefore it is manifestly intended that the invention be limited only by the scope of the claims and equivalence thereof.

We claim:

1. A dental vacuum system for processing effluent from a dental operatory, which comprises:

a cylindrically-shaped vessel having a conically-shaped bottom member defining a separation chamber and including a lid member positioned on said cylindrically-shaped vessel thereby enclosing said separation chamber, a first conduit member horizontally mounted to said cylindrically-shaped vessel proximate said lid member and having an exit port disposed in a horizontal plane facing said lid member, an outlet conduit in gaseous communication with said first conduit member, a second fluid conduit member horizontally mounted to said cylindrically-shaped vessel and vertically disposed below said exit port of said first conduit member for introducing said effluent into said separation chamber, a third conduit member mounted to said conically-shaped bottom member, and means for sealing said exit port of said first conduit member in response to liquid in said separation chamber reaching a predetermined level thereby to prevent liquid from entering said first conduit member; and a side channel two stage blower having a suction side and a vent line to atmosphere, said suction side being in gaseous communication via said outlet conduit in gaseous communication with said first conduit member.

2. The dental vacuum system as defined in claim 1 wherein said blower has an open impeller producing usable flow at 12 inches of Hg. with a maximum vacuum at 17 inches of Hg. at no flow.

3. The dental vacuum system as defined in claim 1 wherein said means for sealing said exit port is comprised of a pivot member having a float member and a sealing member positioned on opposite leg portions of said pivot member, said sealing member including a seal for sealing cooperation with said exit port of said first conduit member.

4. The dental vacuum system as defined in claim 1 wherein said pivot member is mounted to said first conduit member.

5. The dental vacuum system as defined in claim 1 wherein said float member is responsive to a foam level with said separation chamber.

6. The dental vacuum system as defined in claim 1 wherein said outlet conduit in gaseous communication with said first conduit member and said suction side of said blower is provided with a vacuum relief valve.

7. The dental vacuum system as defined in claim 1 wherein said second conduit member includes a solids collection member.

8. A separation apparatus for processing an effluent from a dental operatory, which comprises:

a cylindrically-shaped vessel having a conically-shaped bottom member defining a separation chamber;

a lid member positioned on said cylindrically-shaped vessel thereby enclosing said separation chamber;

a first conduit member horizontally mounted to said cylindrically-shaped vessel proximate said lid member and having an exit port disposed in a horizontal plane facing said lid member;

a second conduit member horizontally mounted to said cylindrically-shaped vessel and vertically disposed below said exit port of said first conduit member for introducing said effluent into said separation chamber;

an outlet conduit in gaseous communication with said first conduit member;

a third conduit member mounted to said conically-shaped bottom member;

an outlet conduit in fluid communication with said third conduit member; and means for sealing said exit port of said first conduit member in response to liquid in said separation chamber reaching a predetermined level thereby to prevent liquid from entering said first conduit member.

9. The separation apparatus as defined in claim 8 wherein said means for sealing said exit port is comprised of a pivot member having a float member and a sealing member positioned on opposite leg portions of said pivot member, said sealing member including a seal for sealing cooperation with said exit port of said first conduit member.

10. The separation apparatus as defined in claim 8 wherein said pivot member is mounted to said first conduit member.

11. The separation apparatus as defined in claim 9 wherein said float member is responsive to a foam level with said separation chamber.

12. The separation apparatus as defined in claim 9 wherein said second conduit member is tangentially mounted to said separation chamber.

* * * * *